United States Patent
Nickel et al.

(10) Patent No.: US 10,888,247 B2
(45) Date of Patent: Jan. 12, 2021

(54) LINEAR PHASE-CORRECTED LOCAL AVERAGING OF MR IMAGE DATA

(71) Applicant: Siemens Healthcare GmbH, Erlangen (DE)

(72) Inventors: Marcel Dominik Nickel, Herzogenaurach (DE); Alto Stemmer, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/522,707

(22) Filed: Jul. 26, 2019

(65) Prior Publication Data

US 2020/0029854 A1   Jan. 30, 2020

(30) Foreign Application Priority Data

Jul. 26, 2018  (DE) .................. 10 2018 212 481

(51) Int. Cl.
*A61B 5/055* (2006.01)
*G01R 33/56* (2006.01)
(Continued)

(52) U.S. Cl.
CPC .......... *A61B 5/055* (2013.01); *G01R 33/5602* (2013.01); *G01R 33/5608* (2013.01);
(Continued)

(58) Field of Classification Search
CPC ............ G01R 33/5602; G01R 33/5608; G01R 33/56509; G01R 33/4804; G01R 33/5611;
(Continued)

(56) References Cited

U.S. PATENT DOCUMENTS 7,999,545 B2 * 8/2011 Ullmann ............ G01R 33/5612
324/314
2011/0234221 A1   9/2011 Feiweier
(Continued)

FOREIGN PATENT DOCUMENTS

DE   102010012948 B4   4/2012
DE   102013201616 B3   7/2014
DE   102015205693 A1   10/2016

OTHER PUBLICATIONS

Newbould, R.D. et al.: "On the utility of complex-averaged diffusion-weighted images"; in: Proc. Intl. Soc. Mag. Reson. Med.; vol. 16; p. 1810; 2008.
(Continued)

*Primary Examiner* — Gregory H Curran
(74) *Attorney, Agent, or Firm* — Schiff Hardin LLP (57) ABSTRACT

In a method for filtering magnetic resonance (MR) image data, complex MR image data is acquired from a region to be imaged, and a sliding window averaging is applied to the complex MR image data to generate filtered MR image data. For each window position of the sliding window averaging: a phase variation of the complex MR image data of individual image points of a sliding window is estimated with a model using a linear phase progression, and filtered complex MR image data is generated based on the estimated phase variation of the complex MR image data. The generation of the filtered complex MR image data uses an average formation of the complex MR image data of the individual image points of the sliding window.

19 Claims, 5 Drawing Sheets

(51) Int. Cl.
*G01R 33/565* (2006.01)
*G01R 33/563* (2006.01)
*G01R 33/561* (2006.01)
*G01R 33/48* (2006.01)

(52) U.S. Cl.
CPC .... *G01R 33/56509* (2013.01); *G01R 33/4804* (2013.01); *G01R 33/5611* (2013.01); *G01R 33/56316* (2013.01); *G01R 33/56341* (2013.01)

(58) Field of Classification Search
CPC ........ G01R 33/56316; G01R 33/56341; A61B 5/055
See application file for complete search history.

(56) References Cited

U.S. PATENT DOCUMENTS

| | | | |
|---|---|---|---|
| 2012/0220858 A1* | 8/2012 | Carroll | G01R 33/5616 600/420 |
| 2014/0203808 A1* | 7/2014 | Hwang | G01R 33/565 324/318 |
| 2014/0210471 A1 | 7/2014 | Stemmer | |
| 2016/0291113 A1 | 10/2016 | Stemmer | |

OTHER PUBLICATIONS

Walsh, D. O. et al.: "Adaptive Reconstruction of Phased Array MR Imagery"; in: Magnetic Resonance in Medicine, vol. 43, pp. 682-690; Wiley-Liss; 43; 2000.
German action dated Jun. 25, 2019, in Application No. 10 2018 212 481.7.

\* cited by examiner

LINEAR PHASE-CORRECTED LOCAL AVERAGING OF MR IMAGE DATA

CROSS REFERENCE TO RELATED APPLICATIONS

This patent application claims priority to German Patent Application No. 102018212481.7, filed Jul. 26, 2018, which is incorporated herein by reference in its entirety.

BACKGROUND

Field

The disclosure relates to a method for filtering magnetic resonance image data. The disclosure also relates to a magnetic resonance (MR) imaging method. The disclosure further relates to an MR image data filter. The disclosure further relates to an MR imaging system.

Related Art

In the creation of magnetic resonance recordings, the body to be examined is exposed to a relatively strong main magnetic field, for example 1.5 tesla, 3 tesla or in newer high magnetic field systems, even 7 tesla. Then, using a suitable antenna device, a high frequency excitation signal is emitted which causes the nuclear spin of particular atoms excited into resonance by this high frequency field in the magnetic field provided to be tilted through a particular flip angle relative to the magnetic field lines of the main magnetic field. The high frequency signal emitted during the relaxation of the nuclear spin, the "magnetic resonance signal" is then received with suitable antenna devices which can also be identical to the transmitting antenna devices. The raw data thereby acquired is finally used to reconstruct the desired image data. For positional encoding, defined magnetic field gradients are overlaid onto the main magnetic field during the transmission and the reading or receiving of the high frequency signals.

Reconstructed MR image data is initially complex variables, i.e. a signal with a complex value is assigned to a pixel or voxel. Due to the complex representation of the image data, a two-dimensional magnetization at the time point of the occurrence of the echo generated by high-frequency signals is described. The two-dimensional magnetization occurs in the x-y plane, i.e. perpendicularly to the static magnetic field applied in the z-direction. However, the measured phase value, that is to say the imaginary part of an MR signal is less informative, since it is determined by unknown influences, for example, the phases of the HF excitation pulses and parameters of the unknown receiving coil. For this reason, in order to obtain MR image data, the value is usually formed from the aforementioned complex variable. However, relative phases, that is to say phase changes are used for applications such as flow determination, diffusion imaging or thermometry.

Diffusion imaging makes diffusion processes visible. The diffusion thereby describes the stochastic temporal behavior of the proton distribution at the subpixel level.

Diffusion-weighted magnetic resonance recordings are magnetic resonance recordings with the aid of which the diffusion movement of particular substances, in particular water molecules, in the body tissue can be measured and represented in a spatially resolved manner. Diffusion imaging has become established in clinical routine, particularly for stroke diagnosis, since the brain regions affected can be recognized earlier in diffusion-weighted images than in classical magnetic resonance recordings. Additionally, diffusion imaging is also used to an increasing extent in the fields of oncological, cardiological and musculoskeletal diseases. A variant of diffusion-weighted magnetic resonance tomography is diffusion tensor imaging in which the direction-dependence of the diffusion is also acquired. In the following, diffusion-weighted magnetic resonance recordings comprise both magnetic resonance recordings generated in the context of diffusion-weighted magnetic resonance tomography and also magnetic resonance recordings created in the context of diffusion tensor imaging.

For the generation of diffusion-weighted magnetic resonance recordings, initially, diffusion-encoded raw data must be acquired. This takes place with special scan sequences which in the following are designated diffusion gradient scan sequences. It is characteristic in these scan sequences that following a typical deflection of the spin into a plane perpendicular to the main magnetic field of the magnetic resonance scanner, a particular sequence of gradient magnetic field pulses is switched which vary the field strength of the outer magnetic field in a specified direction. In the presence of a diffusion movement, the precessing nuclei come out of phase, which is detectable in the scan signal.

During diffusion imaging, typically, a plurality of images with different diffusion directions and weightings, i.e. with different diffusion-encoding gradient pulses are recorded and combined with one another. The strength of the diffusion weighting is usually defined by the "diffusion weighting factor", also called the "b-value". The different diffusion images or the images or parameter maps combined therefrom can then be used for the desired diagnostic purposes. In order to be able to estimate correctly the influence of the diffusion movement, for comparison in many cases a further reference recording is used in which no diffusion encoding gradient pulse is switched, i.e. an image with b=0. The pulse scan sequence for acquiring the reference raw data is constructed in the same way as the diffusion gradient scan sequence with the exception of the emission of the diffusion-encoding gradient pulses. Alternatively, a reference recording can also be carried out with a b-value≠0.

For diagnosis, in the case of MR diffusion imaging, typically images or parameter maps are used for which a free diffusion process, also designated a free normal Gaussian diffusion process with an apparent diffusion coefficient (ADC) is assumed. This process is characterized in that, dependent upon the diffusion weighting factor, the signal strength decreases according to an exponential relationship.

In diffusion imaging, the gradients that are by far the strongest are used in the magnetic resonance imaging between the playing out of the HF excitation signal and the echo signal in order to reduce the MR signal obtained as much as possible dependent upon the diffusion properties of the medium. In this way, a particularly strong image contrast can be created. By contrast therewith, the gradient field strength in static regions has no influence on the signal phase, since there, ideally, a dephasing is entirely reversed by the refocusing signal that is played out. Because of the strong gradients used, diffusion imaging is highly movement-sensitive. The stronger the magnetic field gradients that are used, the greater is this movement sensitivity.

Severely diffusion-weighted MR image data has a low signal-to-noise ratio. In order to obtain more reliable data, the MR scans are therefore repeated several times and average values calculated. With conventional averaging, due to the particularly great movement sensitivity of the phase, a magnitude formation is carried out. However, the magnitude averaging in regions with a very low signal has the disadvantage that it is not central and is therefore subject to Rician noise.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure.

In one or more exemplary embodiments, a "sliding window processing" (abbreviated SWP) is used for averaging. In the SWP, for an image point or pixel or voxel of a region to be imaged, only a small subregion, i.e. the surroundings of this image point, is considered. These surroundings can include, for example, a square and a cuboid of pixels with an odd edge length, wherein the image point under observation lies in the center of the square or the cuboid. Therefore a discretized d-dimensional image with a value range W is associated with an image point x, which can be expressed with the following mapping:

$$X \to W^1 x \ldots x W^d. \tag{1}$$

d can have the value 2 or 3, for example, but is not limited thereto.

At the edge of an image, the excision of the window must be adapted to the edge situation. For example, for this purpose, different edge conditions can be used, for example mirroring at the edge, continuing the edge constantly or displacing the surroundings into the image volume so that the image point no longer lies in the center of the window. Since, with a sequential procedure, the window moves over the image region to be reproduced in a stepwise manner, on the transition to the next image point, it is always only the edge values lying in the movement direction in the window that must be replaced, so that calculation effort can be spared.

In order to carry out an averaging, additionally N repetitions of the scans must be carried out. These can be regarded as a further dimension of the representation describing the averaging process. In formal terms, the following mapping can be defined:

$$F: x \to A_{y,n}, \tag{2}$$

where y extends in a fixed known sequence through the window from x and n is the index of the repetitions.

The size of the window is selected so that it is large enough to be able to utilize a correlation between adjacent pixels. This is possible due to weakly varying parameters, for example with weakly varying phases. On the other hand, the selected window should be small enough so that the enforced correlation is approximately fulfilled. During an averaging of a complex variable, the number of the pixels in a window is somewhat greater than the number of averagings.

A window-based averaging method for determining average values is singular value decomposition as a weighted averaging with local phase-correction.

The averaging can be represented as follows:

$$A_{y,n} = e^{i\varphi_n} B_y.$$

$B_y$ is the desired averaging divided by a phase factor with the value 1. The singular value decomposition of $A_{y,n}$ is given by:

$$A_{y,n} = \left(\frac{B_y}{\|B\|}\right) \begin{pmatrix} \|B\| & \cdots & 0 \\ \vdots & 0 & \vdots \\ 0 & \cdots & 0 \end{pmatrix} \left( \begin{pmatrix} e^{-i\varphi_1} & \cdots \\ \vdots & \cdots \\ e^{-i\varphi_N} & \cdots \end{pmatrix} \right)^+ = U\Sigma V^+. \tag{4}$$

From this, the averaging is obtained as follows:

$$x \to A_{y,n} \to U_{x,1}\Sigma_{11} \to |U_{x,1}\Sigma_{11}|. \tag{5}$$

The two vertical bars in formula (5) are to be understood as magnitude formation. An average is assigned to the value x through the selection of the largest singular value.

This can be understood as a weighted average, since $$U_{x,1}\Sigma_{11} = \Sigma_n A_{x,n} V_{n,1}. \tag{6}$$

From the singular value decomposition, therefore, the weighting coefficients $V_{n,1}$ which also contain the phase correction are obtained. If $A_{y,n}$ does not have precisely the rank 1, then the dominant contribution is projected out. In an exemplary embodiment, to calculate the dominant singular value, the power iteration based on the Krylov method is used.

However, the assumption that the phases do not vary within the window is not always sufficient. For example, this does not apply for diffusion-weighted imaging of the abdomen. The phase variations from breathing and heart movements are too severe even with small windows of the size 5×5 pixels, so that artifacts arise.

It is therefore an object of the present disclosure to develop a method and a device with which movement-related artifacts can be reduced.

In a method for filtering MR image data according to an exemplary embodiment, initially complex MR image data is received. The complex MR image data comprises image information relating to a region of an examination object, for example, a patient, that is to be imaged. As previously mentioned, complex MR image data is based on a two-dimensional magnetization in the region to be imaged at the time point of the detected echo signal. Such MR images are reconstructed on the basis of MR raw data. Such a reconstruction is based on a Fourier transform from k-space of the raw data into the position space. Sliding window averaging ("sliding window processing") is applied to the complex MR image data, as already stated above in relation to the fundamental procedure. However, for each window position, a phase variation of the complex MR image data of individual image points of the sliding window is estimated using a model using a linear phase progression, and filtered complex MR image data of individual image points of the sliding window is generated by average formation of the complex MR image data of individual image points of the sliding window, taking account of the estimated phase variation, i.e. on the basis of the image data corrected by the linear phase variation. In contrast to the conventional sliding window averaging, therefore, a linearly progressing phase variation in a window region is assumed and for the average formation in the context of the sliding window averaging, is based upon correspondingly corrected image data. Advantageously, in this way with the use of strong gradient fields, as are needed, in particular for MR diffusion imaging, an improved robustness of the image data can be achieved as compared with movements of the region to be imaged. For example, movement artifacts can be reduced on the basis of breathing movements or heart movements in diffusion image data.

In the MR imaging method according to an exemplary embodiment, initially, raw data is acquired multiple times from a region to be imaged. That is, a plurality of sets of raw data is generated from the same region to be imaged. Then, on the basis of the acquired raw data, MR image data is reconstructed. Furthermore, a model-based estimation of a phase variation of the complex MR image data of individual image points of a window takes place using a linear phase progression. Finally, filtered complex MR image data is generated by average value formation of the complex MR image data of individual image points of the window taking account of the estimated phase variation. The MR imaging method shares the advantages of the method for filtering MR image data.

In an exemplary embodiment, the MR raw data is obtained by partial sampling of k-space. Furthermore, the non-sampled sub-regions of k-space are filled with zero values. Non-sampled subregions of k-space should be understood as those portions of k-space which in the partial sampling are intentionally not sampled. On the basis of the acquired MR raw data, a reconstruction of image data is carried out. The filling of k-space with zero values corresponds in k-space to the multiplication of the Fourier transform by a window function or, in the image data space, the convolution of the image data with a window function. Thereby, the image is asymmetrically edge-enhanced by the imaginary part of the window function and low-pass filtered by the real part of the window function. Then a filtration of the image data takes place. With the aid of the filtration of the MR image data, the imaginary part of the window function is suppressed in order to compensate for the asymmetrical edge enhancement. In order also to suppress the undesirable low-pass filtration that leads to a blurring of subregions of the image recording, a high-pass filter with an inverse effect to that of the low-pass filter of the window function is also applied to the filtered complex MR image data.

Therefore, the assumption of a local linear variation of the phase values can also advantageously be used for an MR image recording with an acquisition of raw data with a partial sampling of k-space for improving the image quality.

Scan methods with a partial sampling of k-space use the fact that image data in the case of a known phase after phase correction are real-valued and the Fourier transform is combined symmetrically with point-mirroring at the origin combined with the conjugate. There are therefore imaging methods, in which k-space is only partially sampled and the entire image is obtained using phase correction and mirroring in k-space.

However, these procedures are not robust, particularly for diffusion imaging, and show artifacts. The main reason for that is presumably very severe phase variations. If a conventional reconstruction takes place on the basis of partially acquired k-space data in that as already described, non-measured values are filled with zero values, then an effect arises for image reconstruction which can be described mathematically as multiplication of the Fourier transform by a window function in k-space and thus a convolution of the image with a window function in the image data space. The window function is strongly localized and leads to a blurring of the reconstructed image.

The window function can be described, for the event of a partial sampling in a direction $e_j$ as is the case for a diffusion imaging, as follows:

$$f(x)=(f_{real}(x_j)+if_{imag}(x_j))\Pi_{k\neq j}\delta_{x_k,0}, \qquad (7)$$

where $f_{real}(x_j)$ is symmetrical and $f_{imag}(x_j)$ is antisymmetric. The function described has the effect that the real part is low-pass filtered in the j-direction and the imaginary part is asymmetrically edge-enhanced. Both lead to image artifacts which are preferably prevented.

As already mentioned, in order to reduce artifacts, it is possible to carry out an operation in the region of the window of the window function with which the imaginary part is suppressed and subsequently to carry out an operation on the complex combined image by which the effect of the low-pass filter $f_{real}(x_j)$ is compensated. An inverse high-pass filter can easily be used for this purpose. In order to suppress the imaginary part, the linear phase correction which compensates for a part of the edge enhancement can now be used. Advantageously, image artifacts, in particular a blurring of image details, are reduced.

In addition to the linear phase correction, in an image recording with partial sampling of k-space, a global phase correction can also be used in the context of the window-by-window averaging of the image data. Thereby, the global phase for each repetition n is selected so that the total of the intensities in the window is positive. Thereafter, a real-value singular value decomposition can be used in order to obtain a combined image, wherein the imaginary part is either discarded or is interpreted as further real-value image points. Finally, the inverse high-pass filter is applied to the combined image.

In an exemplary embodiment, the MR image data filter includes a phase-corrector configured to determine a corrected phase of complex MR image data applying a sliding window averaging to the complex MR image data. The phase corrector is configured such that for each window position, a phase variation of the complex MR image data of individual image points of the sliding window is estimated with a model using a linear phase progression. In an exemplary embodiment, the MR image data filter also includes an average calculator which is configured to generate filtered complex MR image data through average value formation of the complex MR image data of individual image points of the sliding window taking account of the estimated phase variation. That is, the average formation takes place on the basis of complex image data corrected with the aid of the estimated linear phase variation. The MR image data filter shares the advantages of the method for filtering MR image data.

In an exemplary embodiment, the MR imaging system comprises the MR image data filter. The MR imaging system shares the advantages of the MR image data filter.

In an exemplary embodiment, the MR image data filter is configured as software components. In this embodiment, the some or all of the reconstructor and/or the filter are configured as software. Fundamentally however, these components can also in part be realized, in particular if particularly rapid calculations are involved, in the form of software-supported hardware, for example, FPGAs or the like. Similarly, the required interfaces can be configured, for example, where only an acceptance of data from other software components is concerned, as software interfaces. However, they can also be configured as interfaces constructed from hardware, which are controlled by suitable software.

A realization partially through software has the advantage that computer systems already used in an MR imaging system to date can also easily be upgraded with a software update in order to operate in the manner according to the disclosure. In this respect, the object is also achieved by a corresponding computer program product with a computer program which is loadable directly into a storage apparatus of such a computer system, having program portions in order to carry out all the steps of the method according to the disclosure when the computer program is executed in the computer system.

Such a computer program product can comprise, where relevant, in addition to the computer program, further constituents, such as, for example, documentation and/or additional components including hardware components, for example, hardware keys (dongles, etc.) in order to use the software.

For transport to the controller of the computer system and/or for storage at the computer system, a computer-readable medium, for example, a memory stick, a hard disk or another transportable or permanently installed data carrier can be used on which the program portions of the computer program which are configured to be read in and executed by a computer are stored. For this purpose, the computer can have, for example, one or more cooperating microprocessors or the like.

The dependent claims and the description below each contain particularly advantageous embodiments and developments of the disclosure. In particular the claims of one claim category can also be developed similarly to the dependent claims of another claim category and the description passages belonging thereto. In addition, in the context of the disclosure, the different features of different exemplary embodiments and claims can also be combined to form new exemplary embodiments.

In an exemplary embodiment of the method for filtering MR image data, for each window position, a local constant phase value is determined and for each image point, a phase value is determined for the generation of the filtered complex MR image data, which phase value is formed from a sum of the constant phase value and a value of the estimated phase variation. Thus in this variant a constant phase value valid for the whole window is determined and a variable portion of the phase which is different for each image point of the window. The constant phase portion that is locally valid for the whole window must advantageously be determined only once per window or window position.

In an exemplary embodiment of the method for filtering MR image data, the locally constant phase value is determined using a weighted averaging singular value decomposition of the image data of individual image points of the sliding window. As previously stated in the introduction to the description, from singular value decomposition, weighting coefficients are obtained which specify a local phase correction that applies for the entire window. This procedure can also be considered as a projection of the dominant contribution of the matrix $A_{y,n}$ of the scan values of a window. Since it is sufficient to calculate the dominant eigenvalue, as a numerical value, power iteration, also known as the Krylov method, is used in an exemplary embodiment. Advantageously, the calculation of the phase of image data average values can be simplified and accelerated.

In an exemplary embodiment of the method for filtering MR image data, initially a real-value averaging takes place using singular value decomposition, i.e. the real part and the imaginary part of the image data are handled with separate indices. In this case, the phases of the image data are corrected using the described estimation of the phase variation such that an averaged image intensity is real-valued in one window, i.e. the phase of the averaged image data in one window disappears.

The locally constant phase value, in this case the value "0" is determined as the phase of the average value of the signal intensities determined in one window.

In an exemplary embodiment of the method for filtering MR image data, the complex MR image data comprises diffusion-weighted MR image data. As mentioned above, strong gradients are applied in the diffusion imaging method in order to obtain the most pronounced phase contrast possible. In this example, the image data becomes particularly movement-sensitive, and movement artifacts are easily produced. These artifacts can be reduced by the local linear phase correction.

In an exemplary embodiment, the estimation of a phase variation comprises the determination of a phase term in a plurality of spatial directions. If sampling is carried out slice-by-slice, the sliding window used comprises a window area in the x-y plane. In this event, a phase variation in the x-direction and in the y-direction must be determined. If the windows are defined as three-dimensional sub-volumes, then a phase variation in the z-direction must additionally be determined. For example, in the determination of the local phase variation, a pixel spacing in the j-th direction is considered. The signal intensity $a_{j,n} \cdot e^{i\Delta_{j,n}}$ is given by:

$$a_{j,n} \cdot e^{i\Delta_{j,n}} = \sum_{z \in U_j} A_{z + e_{j,n}} A_{z,n}^*. \tag{8}$$

Here, $U_j$ is the quantity of the pixels in the window for which $z + e_j$ also lies within the window. Furthermore, $a_{j,n}$ and $\Delta_{j,n}$ are real-valued, so that in particular $\Delta_{j,n}$ simply corresponds to the phase of the sum.

The linear phase correction for the signal values $A_{x,n}$ in the window is then given by:

$$A_{x,n} \rightarrow A_{x,n} e^{-i\Sigma_{j=1}^{d} \Delta_{j,n} x_j}. \quad (9)$$

This correction arises therefrom that a signal with an actually linearly progressing phase of the form:

$$A_{x,n} \rightarrow M_n e^{i\Sigma_{j=1}^{d} \Delta_{j,n} x_j} \quad (10)$$

would be exactly corrected and this sum is intensity-weighted.

Furthermore, weights $V_{n,1}$ determined during the signal value determination can be used to determine image data corrupted by movement and to separate it out during the reconstruction. Apart from the phase variation, a movement during the diffusion imaging also causes a signal obliteration resulting from a dephasing within a voxel. For example, during abdominal diffusion imaging, a region of the left liver lobe is almost completely obliterated in the image data during a heartbeat. For this reason, an averaged image in which individual image recordings are corrupted has very low signal intensity.

In order to separate out the corrupted image data, the contributions of the determined weights $V_{n,1}$ of the singular value decomposition can be observed. If no corruption has taken place, then weights all have the same value:

$$|V_{n,1}| = \frac{1}{\sqrt{N}}. \quad (11)$$

In the event that some images are corrupted, the entries of the weightings of the corrupted images are significantly smaller, i.e.

$$|V_{n,1}| << \frac{1}{\sqrt{N}}. \quad (12)$$

Therefore, at an image position x, the number of the indices n for which the weights lie below the threshold can be determined through knowledge of the number of repetitions N of the image recordings and by specifying a threshold value. In this way, a number $N_{eff}(x)$ of the effective uncorrupted image data can be determined at each pixel. Due to the spatial correlation of the corruption of the images, spatial average values $$\overline{N_{eff}}$$

can be calculated over a whole window in each case. Such average values can be calculated, for example, using a statistically robust means, such as a median filter. Finally, a correction factor $$\frac{N}{\overline{N_{eff}}}$$

is obtained, by which the image intensity can be corrected in order to compensate for the corruption. Advantageously, in this way, a reduction of the image intensity due to signal dropout in individual image recordings can be prevented.

In place of a threshold, other images can be used for determining the effective number $N_{eff}(x)$ of the uncorrupted image data sets. For example, as a robust means, the median can be calculated and the deviation therefrom can be observed. This process can also take place over a plurality of windows simultaneously in order to reduce the resolution of Neff(x). In this way, the effort involved in data processing in image processing is reduced.

Figure 1:
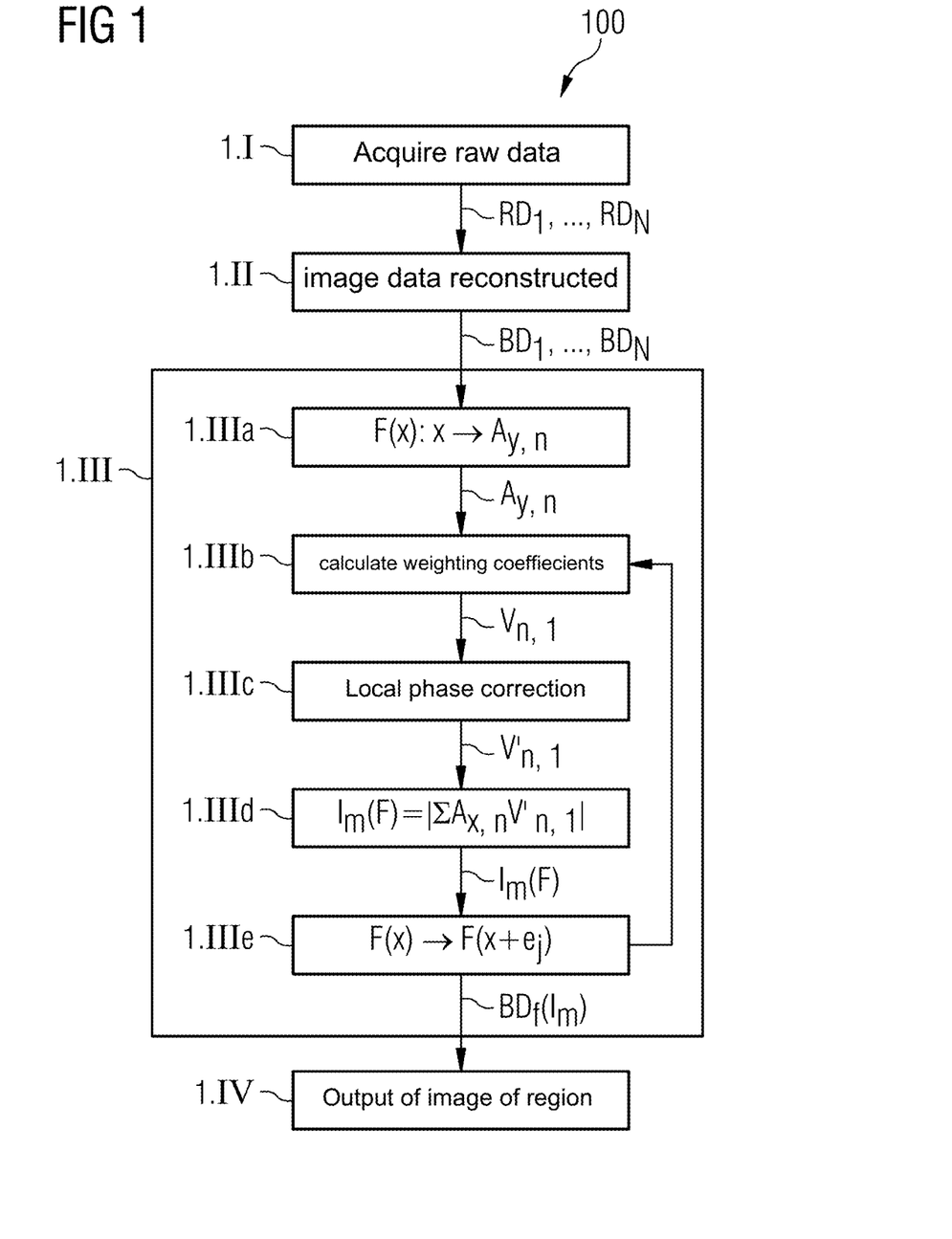
FIG. 1 shows a flow diagram of an MR imaging method according to an exemplary embodiment of the disclosure.
Figure 2:
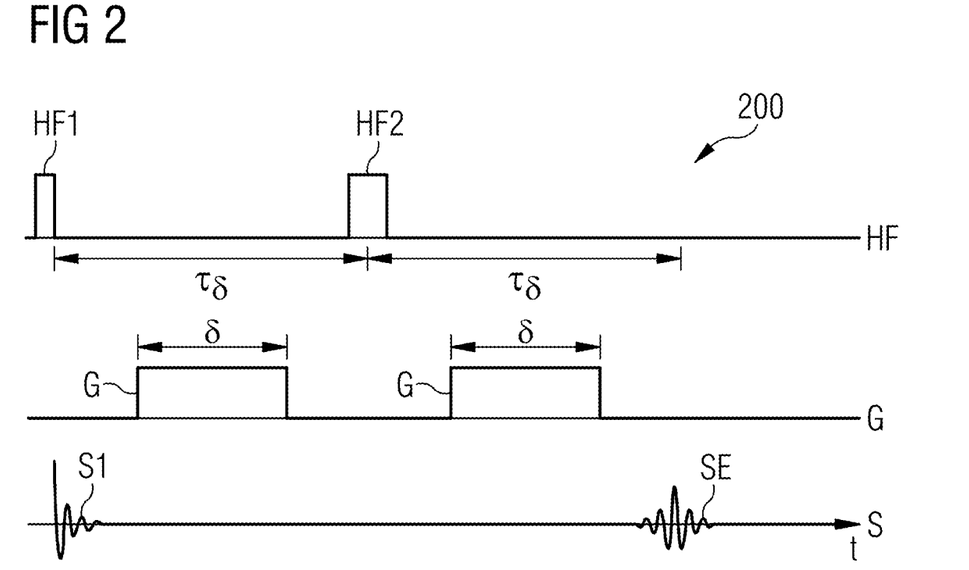
FIG. 2 shows a schematic illustrating a Stejskal-Tanner pulse sequence according to an exemplary embodiment of the disclosure.

FIG. 1 shows a flow diagram 100 which illustrates an MR imaging method according to an exemplary embodiment of the disclosure. In step 1.I, in the context of an MR diffusion imaging process, raw data is acquired from the abdominal region of a patient. A pulse sequence for a diffusion imaging process is shown in FIG. 2. As illustrated in FIG. 2, spin-echo signals attenuated by gradients are compared with non-attenuated spin-echo signals in order to be able to estimate a strength of a diffusion movement. Due to the low signal strength, the acquired scan data is subject to severe noise effects, which leads to statistical uncertainties. Therefore, a multiple (N-fold) repetition of the raw data acquisition takes place, wherein N raw data sets $RD_1, \ldots, RD_n, \ldots RD_N$ are acquired (N is a natural number, $n \in \{1 \ldots N\}$).

In step 1.II, on the basis of the raw data $RD_1, \ldots, RD_N$ complex image data $BD_1, \ldots, BD_n, \ldots, BD_N$ is reconstructed.

Subsequently, the reconstructed image data $BD_1, \ldots, BD_N$ is determined window-by-window in step 1.III. Since for each subregion or window region on the basis of the N-th repetition of the acquisition, N sets of complex image data exist, in each case, at the same time an averaging of the image data over the N image data sets takes place. In step 1.IIIa, initially an area and position x of a window F is defined which is moved stepwise over the region ROI to be imaged. Formally expressed, a representation $A_{y,n}$ is assigned to a pixel point x which comprises the image data or intensities of all the window pixels y for all N repetitions of the image recordings. On the basis of this representation, in step 1.IIIb according to formula (6), weighting coefficients $V_{n,1}$ are calculated which already contain a local phase correction. This is needed since the phases of the image data assume different values in different window regions.

In step 1.IIIc, in addition, a local phase correction takes place within the individual window regions. I.e. the weightings $V_{n,1}$ determined using the singular value decomposition are corrected by a linear factor $e^{-i\Sigma_{j=1}^{d}\Delta_{j,n}x_j}$, by which corrected weightings $V'_{n,1}$ are generated. The variable $\Delta_{j,n}$ is given by equation (8) and $x_j$ represents the individual pixels in the current window region. Furthermore, in step 1.IIId, a weighted averaging of the n representations $A_{x,n}$ determined takes place with the weightings $V'_{n,1}$ according to the formulae (5) and (4). In this way, an averaged pixel intensity $I_m(F)$ is obtained for a predetermined window position. In the step 1.IIIe, the window F is displaced by a predetermined pixel number, for example a single pixel, in a predetermined direction. Subsequently, a return to step 1.IIIb takes place and steps 1.IIIb to 1.IIIe are repeated until the whole region of the patient to be imaged has been sampled and for each window position, an averaged pixel intensity has been calculated. Finally, in step 1.IV, an image of a region ROI to be imaged which comprises the calculated pixel intensities determined is output.

FIG. 2 shows by way of example, a schematic of a Stejskal-Tanner pulse sequence which can be used for the diffusion imaging. In the schematic, arranged over one another are amplitudes of high frequency pulses HF, gradients G and scan signals S, plotted over time t. As already mentioned, a diffusion movement along a gradient field is measured as the attenuation of a spin echo.

A diffusion-weighted MRT pulse sequence begins with a high-frequency signal HF1 being radiated into a region to be imaged so that the sum vector of the magnetization is tilted in the aforementioned region by 90° into the x-y plane. Thereby, due to the change in the magnetization, a first signal S1 is generated through an induction of a corresponding electrical voltage in a measurement coil. The diffusion weighting now takes place in that a briefly switched gradient field G (for the timespan $\delta$) varies the field strength of the outer magnetic field in a predetermined direction. Along this direction, therefore, the Lamor frequency of the atomic nuclei is also varied accordingly. Therefore, the nuclei go out of phase and the voltage S1 induced in the measurement coil disappears. After half the echo time $\tau_\delta$ a radiating-in of a new HF pulse HF2 takes place with which the spin direction of the nuclei is changed by 180° and the same gradient field G is switched in again. On the basis of the identical frequency differences in the reverse rotation direction, the magnetic moments now pass back into phase and again a signal, the spin echo SE, is induced. Due to the diffusion movement, however, this signal SE is weaker than the signal S1 at the start of the pulse sequence. This is because a proportion of the atomic nuclei do not go back into phase since these atomic nuclei have moved in the direction of the gradient field. In order to be able to estimate the influence of a diffusion movement, a comparison with a second image recording without gradients is necessary since other effects such as, for example, spin-spin interactions also weaken the spin-echo SE.

Figure 3:
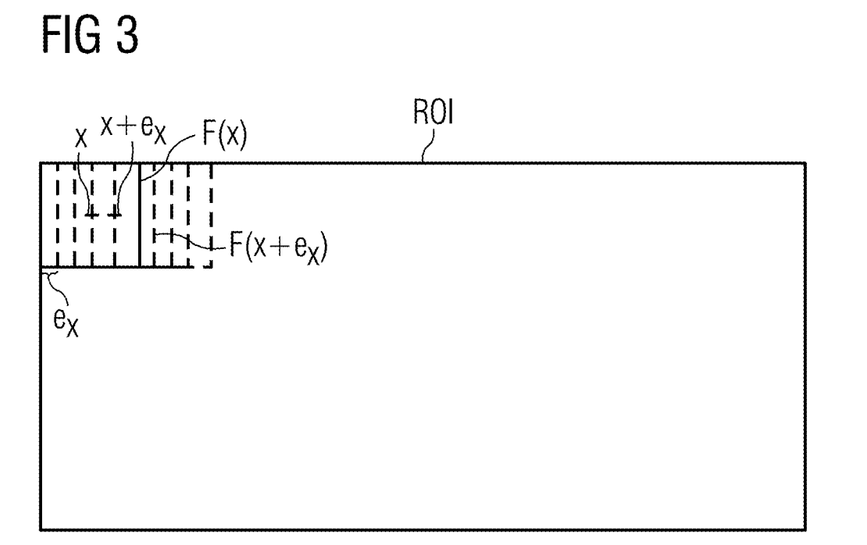
FIG. 3 shows a schematic representation of a window-by-window image recording according to an exemplary embodiment of the disclosure.

FIG. 3 shows, by way of example, a region ROI to be represented, which is imaged with the aid of a window-by-window image reconstruction. The region ROI to be imaged is shown only two-dimensional for simplicity. Shown in the upper left corner of the region ROI to be imaged is a square window F(x) with a solid line round the point x in the region to be imaged. In addition to the pixel at the location x, the window F(x) has further pixels. In total, the window F(x) comprises 25 pixels. In a first reconstruction step, only image data, i.e. intensity values I(F) in the defined window F(x) for each of the 25 pixels is reconstructed. Then an averaging of the reconstructed intensity values is undertaken, so that an averaged intensity value $I_m(F(x))$ is obtained for the window F(x) at the site x. Then, in the context of a sliding window reconstruction, the window F is displaced from the position x to the site $x+e_x$ and now again an image reconstruction of the 25 pixels covered by the newly positioned window $F(x+e_x)$ is carried out. Subsequently, the determined intensity values $I(F(x+e_x))$ are determined again, so that now an averaged intensity value $I_m(F(x+e_x))$ is obtained from the window region displaced by $e_x$. The sliding window processing is continued until the complete region ROI to be imaged has been sampled.

Figure 4:
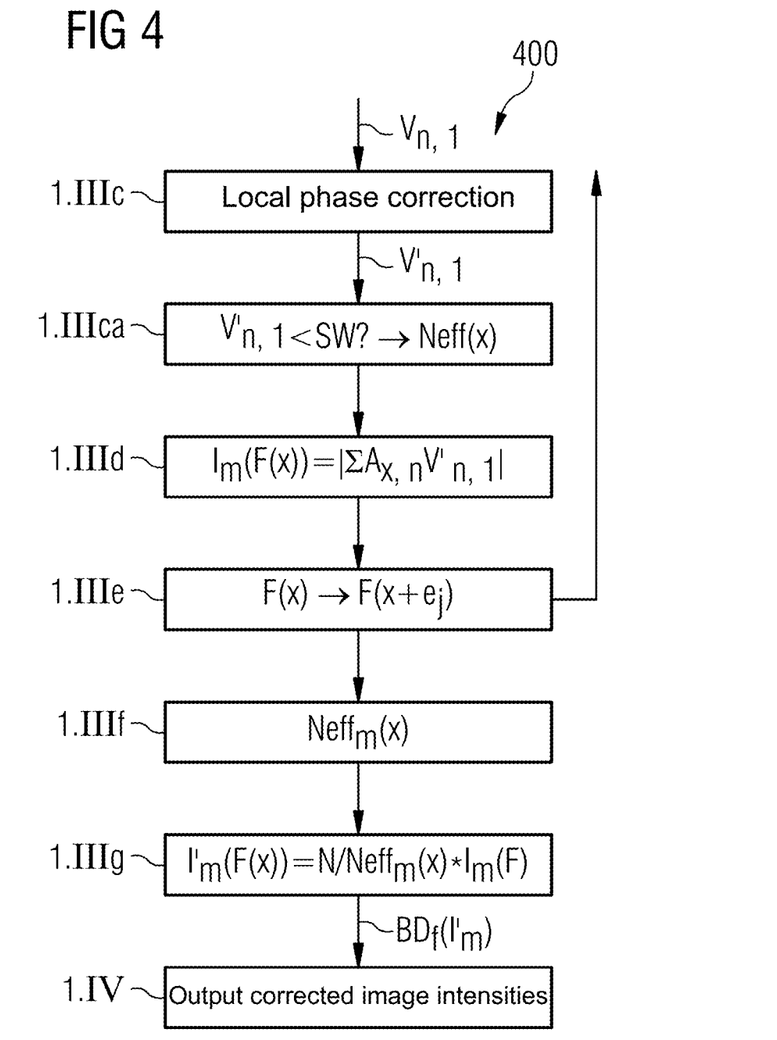
FIG. 4 shows a flowchart of an MR imaging method according to an exemplary embodiment of the disclosure.

FIG. 4 shows a flow diagram 400 which illustrates an MR imaging method according to an exemplary embodiment of the disclosure. For the sake of clarity, the steps 1.I, 1.II, 1.IIIa and 1.IIIb which correspond to the method steps set out in FIG. 1 are not shown. In step 1.IIIc as in the variant shown in FIG. 1, in addition, a local phase correction takes place within the individual window regions. I.e. the weightings $V_{n,1}$ determined using the singular value decomposition are corrected by a linear factor $e^{-i\Sigma_{j=1}^d \Delta_j \cdot x_j}$ and corrected weightings $V'_{n,1}$ are generated. Subsequently, in step 1.IIIca, a test of whether weightings $V'_{n,1}$ exceed a predetermined threshold value SW takes place. This test serves to separate out "corrupted" image data. Such image data arises if, during a diffusion imaging process in a subregion to be imaged, a signal is almost completely extinguished due to a body movement. As a consequence, the reconstructed image which is generated per window from a number N of image reconstructions, has less signal intensity in subregions in which individual instances of these N image data sets are corrupted. In step 1.IIIca, the contributions of the weightings $V'_{n,1}$ determined in the filter process are now investigated as to whether they fall below a threshold value SW. If this is the case, the effective number Neff(x) of the image reconstructions for a pixel x is reduced. Subsequently, in the step 1.IIId, as in the exemplary embodiment illustrated in FIG. 1, a calculation of the image intensities of the pixels x takes place.

In the step 1.IIIe, the window is again displaced by $e_j$ and the reconstruction continues with the steps 1.IIIb to 1.IIId until the complete region ROI to be imaged is reconstructed. In the step 1.IIIf, as distinct from the variant shown in FIG. 1, a determination of a spatially determined map of the number $\text{Neff}_m(x)$ of the effectively uncorrupted images now takes place. This process is therefore useful since corruption is spatially correlated. This step can take place with a statistically robust means such as for example a median filter. In the step 1.IIIg which also differs from the procedure illustrated in FIG. 1, with the aid of the averaged number $\text{Neff}_m(x)$ and the known number N of the acquisition and reconstruction per pixel, image intensities $I'_m(F(x))=N/\text{Neff}_m(x)*I_m(F(x))$ corrected by the loss of the signal intensity are calculated. Finally, in step 1.IV, corrected image data $BD_f(I'_m)$ which comprises the corrected image intensities $I'_m(F(x))$ is output. Therefore, image intensities reduced by movements are corrected, so that the image quality is improved.

Figure 5:
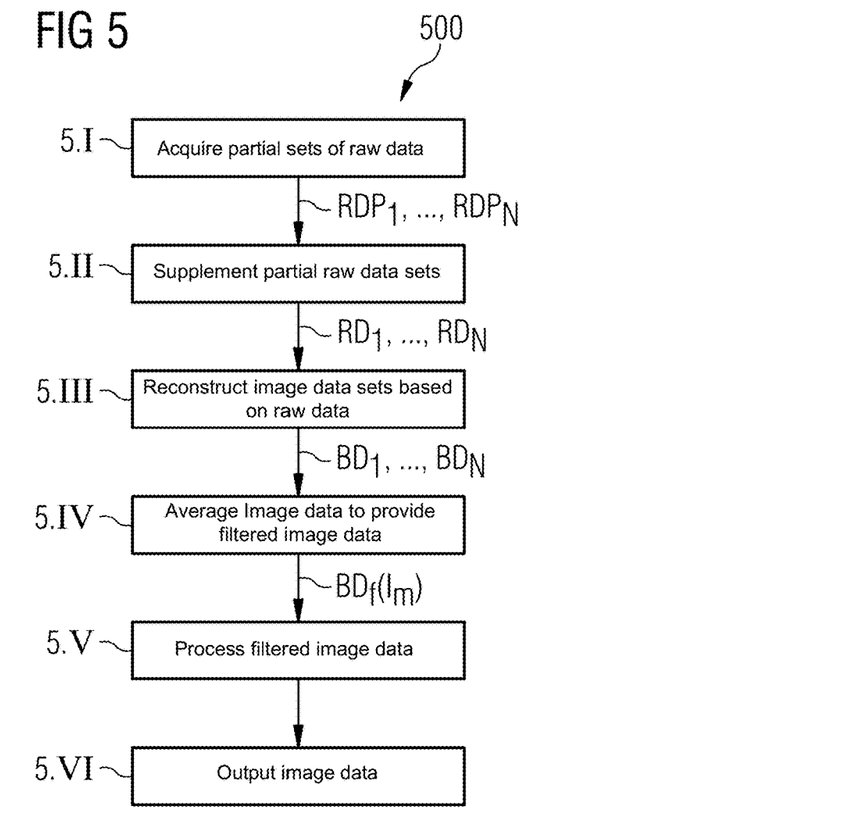
FIG. 5 shows a flowchart of an MR imaging method with partial sampling of k-space according to an exemplary embodiment of the disclosure.

FIG. 5 shows a flow diagram 500 which illustrates an MR imaging method with partial sampling of k-space according to an exemplary embodiment of the disclosure. In a partial sampling, only sampling of a part of k-space takes place, whereby the lacking image information or raw data is determined using phase correction and mirroring in k-space. However, conventional procedures for diffusion imaging are not sufficiently robust, which leads to a severe artifact formation. The cause of the artifacts is probably to be found in a severe phase variation. As already mentioned in the introduction, the non-sampled regions in k-space are filled with zero values. This corresponds to the multiplication of the Fourier transforms by a window function and thereby a convolution of the image with a window function. Due to the strong localization of the window, the reconstructed image is severely blurred. The aforementioned artifacts can be suppressed using a phase correction and a subsequent high-pass filtration.

In step 5.I, initially N partial sets of raw data $RDP_1, \ldots, RDP_N$ are acquired in k-space in the context of a diffusion imaging. The partial raw data sets $RDP_1, \ldots, RDP_N$ are subsequently supplemented in step 5.II with zero values in k-space regions in which k-space has not been sampled and thus complete raw data sets $RD_1, \ldots, RD_N$ are generated. In step 5.III, on the basis of the raw data sets $RD_1, \ldots, RD_N$, N image data sets $BD_1, \ldots, BD_N$ are reconstructed. Then in step 5.IV, an averaging of the image data $BD_1, \ldots, BD_N$ corresponding to step 1.III takes place with a phase correction as has been described, for example, in relation to FIG. 1, in order to compensate for the edge enhancement caused by the partial sampling. The filtered image data $DB_f(I_m)$ thereby arising is processed in step 5.IV with the aid of an inverse high-pass filter which compensates for a low-pass effect created by the real part of the window function. Finally, the image data corrected in this way is output in step 5.VI.

Figure 6:
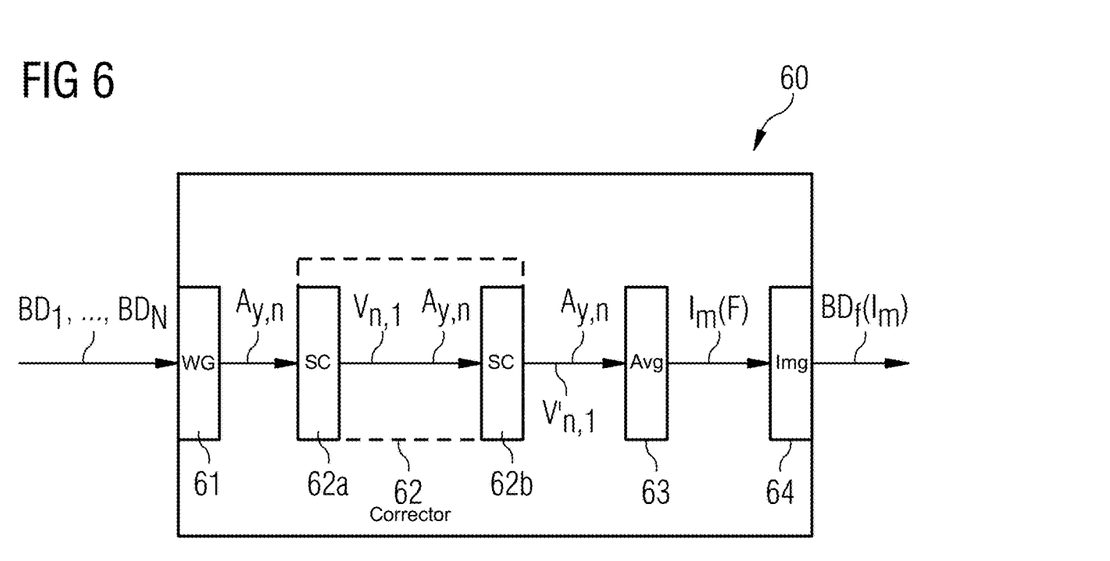
FIG. 6 shows a schematic representation of a filter according to an exemplary embodiment of the disclosure.

FIG. 6 illustrates a filter 60 according to an exemplary embodiment of the disclosure. The filter 60 comprises a window generator 61 which groups received image information $BD_1, \ldots, BD_N$ window-by-window into window image data $A_{y,n}$. The window image data $A_{y,n}$ is transferred to a phase corrector 62 which comprises a first phase sub-corrector 62a and a second phase sub-corrector 62b. The first phase sub-corrector 62a serves to determine, on the basis of a window image data set $A_{y,n}$, a unified phase correction value for the entire window. Hereby, the weighting coefficients $V_{n,1}$ defined in formula (5) are generated. On the basis of the window image data $A_{y,n}$, phase correction values linearly dependent on the position in the window are calculated by the second phase corrector 62b, which values multiplied by the weighting coefficients $V_{n,1}$ calculated by the first phase corrector 62a produce corrected weighting coefficients $V'_{n,1}$. Part of the filter 60 is also an average calculator 63 which calculates, on the basis of the window image data $A_{y,n}$ and the corrected weightings $V'_{n,1}$ for each window F or each window position x, an intensity mean value $I_m(F)$. The intensity mean values are transferred to an image generator 64 which combines therefrom a completely filtered image $BD_f(I_m)$ from a region ROI to be investigated.

Figure 7:
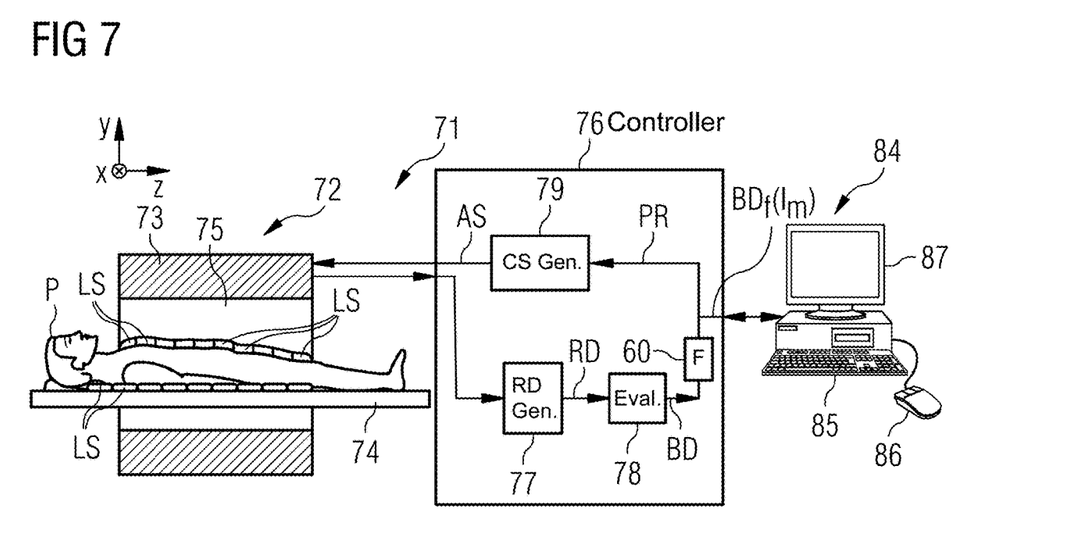
FIG. 7 shows a schematic representation of an MR imaging system according to an exemplary embodiment of the disclosure.

FIG. 7 shows an exemplary embodiment of a magnetic resonance system 71, which is configured to perform the one or more operations of methods 100, 400, and/or 500. In an exemplary embodiment, the core of this magnetic resonance system 71 is the magnetic resonance scanner 72, in which a patient P is positioned on a patient positioning table 74 (also, patient support 74) in a ring-shaped main field magnet 73 which encloses the scanning space 75. Situated on and possibly also under the patient, there are, for example, a plurality of local coils LS, also known as magnetic resonance coils.

The patient support 74 is displaceable in the longitudinal direction, i.e. along the longitudinal axis of the scanner 72. This direction is designated the z-direction in the room coordinate system, which is also shown. Situated within the main magnetic field in the scanner 72 is a whole body coil (not shown in detail), with which the high frequency pulses can be emitted and received. Furthermore, the scanner 72 has, in a conventional manner (not shown in FIG. 7), gradient coils in order to apply a magnetic field gradient in each of the room directions x, y, z.

The scanner 72 is controlled by a controller 76, which here is shown as separate component. A terminal 84 is connected to the controller 76. This terminal 84 has a screen 87, a keyboard 85 and a mouse 86 for a graphical user interface, for example, a mouse 86 or the like. The terminal 84 serves, inter alia, as a user interface by which a user operates the controller 76 and thereby the scanner 72. The controller 76 and/or the terminal 84 can be an integral component of the scanner 72 in one or more aspects. In an exemplary embodiment, the controller 76 includes processor circuitry that is configured to perform one or more functions/operations of the controller 76, including controlling the scanner 72 and generating the filtered image data $BD_f(I_m)$. The controller 76 can provide the filtered image data $BD_f(I_m)$ to the terminal 84. In an exemplary embodiment, the terminal 84 includes processor circuitry that is configured to perform one or more functions/operations of the terminal 84. In an exemplary embodiment, the terminal 84 is a computer that is configured to execute one or more internally and/or externally stored applications/programs to perform the functions/operations of the terminal 84.

The magnetic resonance system 71 can also have all the further usual components and features of such systems, for example, interfaces for connecting a communication network, for example an image information system or the like. However, all these components are not shown in FIG. 7 for sake of greater clarity.

An operator can communicate with the controller 76 using the terminal 84 and so provide for the execution of the desired measurements in that, for example, the scanner 72 is controlled by the controller 76 such that the required high frequency pulse sequences are emitted by the high frequency coils and the gradient coils are switched in a suitable manner. Via the controller 76, the raw data RD coming from the scanner that is needed for the imaging is also acquired. For this purpose, the controller 76 comprises a raw data generator 77 in which scan signals coming from the scanner 72 are converted into raw data RD. For example, this is achieved using a digitization of the scan signals. In a signal evaluator 78, which can be, for example, a module of the controller 76, raw data RD is reconstructed to image data BD. The reconstructed image data BD is further transmitted to a filter 60 which in the exemplary embodiment shown in FIG. 7 is also a part of the controller 76. The filter 60 is constructed as shown in FIG. 6. The filtered image data $BD_f(I_m)$ can be visualized, for example, on the screen 87 of the terminal 74 and/or stored in a memory store or transmitted via a network. Furthermore, the controller 76 has a control sequence generator 79 with which a control sequence AS is generated according to a protocol which is received, for example, by the terminal 84.

For example, from the terminal 84, the control sequence generator 79 receives protocol data PR which has predetermined parameter values of a pulse sequence AS to be determined. The control sequence generator 79 is further configured to play out a control sequence AS on the magnetic resonance scanner 72. This includes, for example, a pulse sequence for a diffusion imaging process.

In an exemplary embodiment, the components of the filter 60 required for implementing the disclosure in a magnetic resonance system 71 are created at least partially or even completely in the form of software components. Typical magnetic resonance systems already have programmable controllers. In such a case, the system according to an exemplary embodiment is realizable in this way with the aid of suitable control software. That is, a suitable computer program is loaded directly into the memory of a programmable controller 76 of the magnetic resonance system 71 in question, which has computer program code to carry out the methods 100, 400, and/or 500 according exemplary embodiments described herein. In this way, already existing magnetic resonance systems are also retrofittable easily and economically.

In particular, it is possible that some of the components are also realized as subroutines in components already existing in the controller 76, or that existing components are also used for the inventive purpose. This concerns, for example, the filter 60 which can be implemented, for example, in an existing controller 76, possibly in an already present reconstructor 78.

Finally, it should again be noted that the methods and devices described above are merely preferred exemplary embodiments of the disclosure and that the disclosure can be modified by a person skilled in the art without departing from the field of the disclosure, insofar as it is specified by the claims. For the sake of completeness, it should also be mentioned that the use of the indefinite article "a" or "an" does not preclude the relevant features from also being present plurally. Similarly, the expression "unit" does not preclude this consisting of a plurality of components which can possibly also be spatially distributed.

CONCLUSION

The aforementioned description of the specific embodiments will so fully reveal the general nature of the disclosure that others can, by applying knowledge within the skill of the art, readily modify and/or adapt for various applications such specific embodiments, without undue experimentation, and without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computers, processors, controllers, or other devices executing the firmware, software, routines, instructions, etc. Further, any of the implementation variations may be carried out by a general purpose computer.

For the purposes of this discussion, the term "processor circuitry" shall be understood to be circuit(s), processor(s), logic, or a combination thereof. A circuit includes an analog circuit, a digital circuit, state machine logic, programmable processing circuit, other structural electronic hardware, or a combination thereof. A processor includes a microprocessor, a digital signal processor (DSP), central processing unit (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A method for filtering magnetic resonance (MR) image data, comprising:
    receiving complex MR image data from a region to be imaged; and
    applying a sliding window averaging to the complex MR image data to generate filtered MR image data, wherein, for each window position of the sliding window averaging:
        estimating, with a model using a linear phase progression, a phase variation of the complex MR image data of individual image points of a sliding window; and
        generating, based on the estimated phase variation of the complex MR image data, filtered complex MR image data using an average formation of the complex MR image data of the individual image points of the sliding window.

2. The method as claimed in claim 1, further comprising:
    determining a locally constant phase value for each window position,
    wherein the generating the filtered complex MR image data comprises, for each of the individual image points, determining a phase value based on a sum of the locally constant phase value and a value of the estimated phase variation.

3. The method as claimed in claim 2, wherein the locally constant phase value is determined based on a weighted averaging singular value decomposition of the complex image data of the individual image points of the sliding window.

4. The method as claimed in claim 2, further comprising performing a singular value decomposition to provide a real-value averaging and determining a phase variation of the complex MR image data such that an average value of the complex MR image data determined in the sliding window is real-valued.

5. The method as claimed in claim 1, wherein the complex MR image data comprises diffusion-weighted MR image data.

6. The method as claimed in claim 1, wherein the estimation of a phase variation comprises determining a phase term in a plurality of spatial directions.

7. The method as claimed in claim 6, wherein the estimation of a phase variation comprises determining a phase variation in an x-direction and in a y-direction that is perpendicular to the x-direction.

8. The method as claimed in claim 7, wherein the estimation of a phase variation further comprises determining a phase variation in a z-direction that is perpendicular to the x-direction and the y-direction.

9. The method as claimed in claim 3, wherein corrupted image data of the complex MR image data is determined based on weights determined from the estimation of the phase.

10. The method as claimed in claim 1, further comprising generating an electronic output signal representing the filtered complex MR image data.

11. A computer program product having a computer program which is directly loadable into a memory of a controller of an MR imaging device, when executed by the controller, causes the MR imaging device to perform the method as claimed in claim 1.

12. A non-transitory computer-readable medium on which computer-executable program portions are stored, that when executed, cause the computer to perform the method as claimed in claim 1.

13. A magnetic resonance (MR) imaging method, comprising:
acquiring MR raw data from a region to be imaged;
reconstructing MR image data based on the acquired MR raw data; and
applying a sliding window averaging to the reconstructed MR image data to generate filtered MR image data, wherein, for each window position of the sliding window averaging:
estimating, with a model using a linear phase progression, a phase variation of the reconstructed MR image data of individual image points of a sliding window; and
generating, based on the estimated phase variation of the reconstructed MR image data, the filtered MR image data using an average formation of the reconstructed MR image data of the individual image points of the sliding window.

14. The MR imaging method as claimed in claim 13, wherein:
the acquisition of the MR raw data comprises partial sampling of k-space, non-sampled sub-regions of k-space being filled with zero values; and
the method further comprises high-pass filtering the filtered MR image data.

15. The MR imaging method as claimed in claim 13, further comprising generating an electronic output signal representing the filtered MR image data.

16. A computer program product having a computer program which is directly loadable into a memory of a controller of an MR imaging device, when executed by the controller, causes the MR imaging device to perform the method as claimed in claim 13.

17. A non-transitory computer-readable medium on which computer-executable program portions are stored, that when executed, cause the computer to perform the method as claimed in claim 13.

18. A magnetic resonance (MR) image data filter, comprising:
a phase corrector configured to apply a sliding window averaging to complex MR image data to determine a corrected phase of the complex MR image data, wherein, for each window position of the sliding window averaging, estimating, with a model using a linear phase progression, a phase variation of the complex MR image data of individual image points of a sliding window; and
an average calculator configured to generate, for each of the window positions and based on a respective one of the estimated phase variations, filtered complex MR image data using an average formation of the complex MR image data of individual image points of the sliding window.

19. A magnetic resonance (MR) imaging system comprising:
the MR image data filter as claimed in claim 18; and
a MR scanner configured to generate MR data from a region to be imaged, the complex MR image data being generated from the MR data provided by the MR scanner.

* * * * *